United States Patent
Gupta et al.

(10) Patent No.: US 11,488,686 B2
(45) Date of Patent: *Nov. 1, 2022

(54) METHOD AND SYSTEM FOR IN SILICO TESTING OF ACTIVES ON HUMAN SKIN

(71) Applicant: Tata Consultancy Services Limited, Mumbai (IN)

(72) Inventors: Rakesh Gupta, Pune (IN); Kishore Gajula, Pune (IN); Balaramasridhar Dwadasi, Pune (IN); Beena Rai, Pune (IN)

(73) Assignee: Tata Consultancy Services Limited, Mumbai (IN)

( * ) Notice: Subject to any disclaimer, the term of this patent is extended or adjusted under 35 U.S.C. 154(b) by 1212 days.

This patent is subject to a terminal disclaimer.

(21) Appl. No.: 15/900,448

(22) Filed: Feb. 20, 2018

(65) Prior Publication Data

US 2018/0253525 A1    Sep. 6, 2018

(30) Foreign Application Priority Data

Mar. 3, 2017 (IN) .............................. 201721007631

(51) Int. Cl.
| | | |
|---|---|---|
| G16B 5/30 | (2019.01) | |
| G16B 5/00 | (2019.01) | |
| G16B 35/00 | (2019.01) | |
| G16C 20/60 | (2019.01) | |
| G16C 20/30 | (2019.01) | |
| G16H 50/50 | (2018.01) | |
| G16C 20/64 | (2019.01) | |
| G16H 50/20 | (2018.01) | |
| G16C 20/10 | (2019.01) | |

(52) U.S. Cl.
CPC ................ *G16B 5/30* (2019.02); *G16B 5/00* (2019.02); *G16B 35/00* (2019.02); *G16C 20/30* (2019.02); *G16C 20/60* (2019.02); *G16C 20/64* (2019.02); *G16H 50/50* (2018.01); *G16C 20/10* (2019.02); *G16H 50/20* (2018.01)

(58) Field of Classification Search
None
See application file for complete search history.

(56) References Cited

U.S. PATENT DOCUMENTS

| | | |
|---|---|---|
| 7,169,382 B2 | 1/2007 | Chopart et al. |
| 2007/0021357 A1 | 1/2007 | Tobia et al. |
| 2011/0098258 A1 | 4/2011 | Masini-Eteve et al. |
| 2016/0184245 A1 | 6/2016 | Eberting |

FOREIGN PATENT DOCUMENTS

| | | |
|---|---|---|
| CA | 2618033 | 12/2005 |
| CN | 101221160 A | 7/2008 |
| WO | WO-2011/016743 A1 | 2/2011 |

OTHER PUBLICATIONS

Marrink et al. J. Phys. Chem. 1996, 100, 16729-16738.*
Gupta et al. J. Phys. Chem. 2015, 119, 11643-11655).*
Rim et. al. Annals of Biomedical Engineering vol. 37, pp. 1217-1229, 2009.*
Rim, J. E. et al. (Jun. 2009) "Multiscale Modeling Framework of Transdermal Drug Delivery" Annals of Biomedical Engineering, vol. 37, No. 6, Jun. 2009, pp. 1217-1229.
Das, C.. et al. (Oct. 2009). " Simulation studies of stratum corneum lipid mixtures" vol. 97, issue 7; pp. 1941-1951, Biophysical Journal.
Höltje, M. et al. (Mar. 2001) "Molecular dynamics simulations of stratum corneum lipid models: fatty acids and cholesterol" Biochimica et Biophysica Acta vol. 1511, No. 1; pp. 156-167—Biomembranes, Volume-issue number(s): Publisher: Elsevier link: https://ac.els-cdn.com/S000527360100270X/1-s2.0-S000527360100270X-main.pdf?_tid=c13d5ad2-0b2f-11e8-ae97-00000aab0f6c&acdnat=1517916217_9bc2ed2cc6ad98a264c4dc6f7a710cb5.

* cited by examiner

*Primary Examiner* — Michael L Borin
(74) *Attorney, Agent, or Firm* — Finnegan, Henderson, Farabow, Garrett & Dunner, LLP

(57) ABSTRACT

A method and system for in-silico testing of actives on human skin is described. The present invention discloses a micro and macroscopic level model of the skins upper protective layer Stratum-Corneum. The invention presents a multi-scale modeling framework for the calculation of diffusion and release profile of different actives like drugs, particles and cosmetics through developed skin model using molecular dynamics simulations and computational fluid dynamics approach. The systems consist of a molecular model of the skin's upper layer stratum corneum and permeate molecules. The system also consists of a macroscopic transport model of stratum corneum. The transport model is used to generate the release profile of the active molecule.

19 Claims, 7 Drawing Sheets

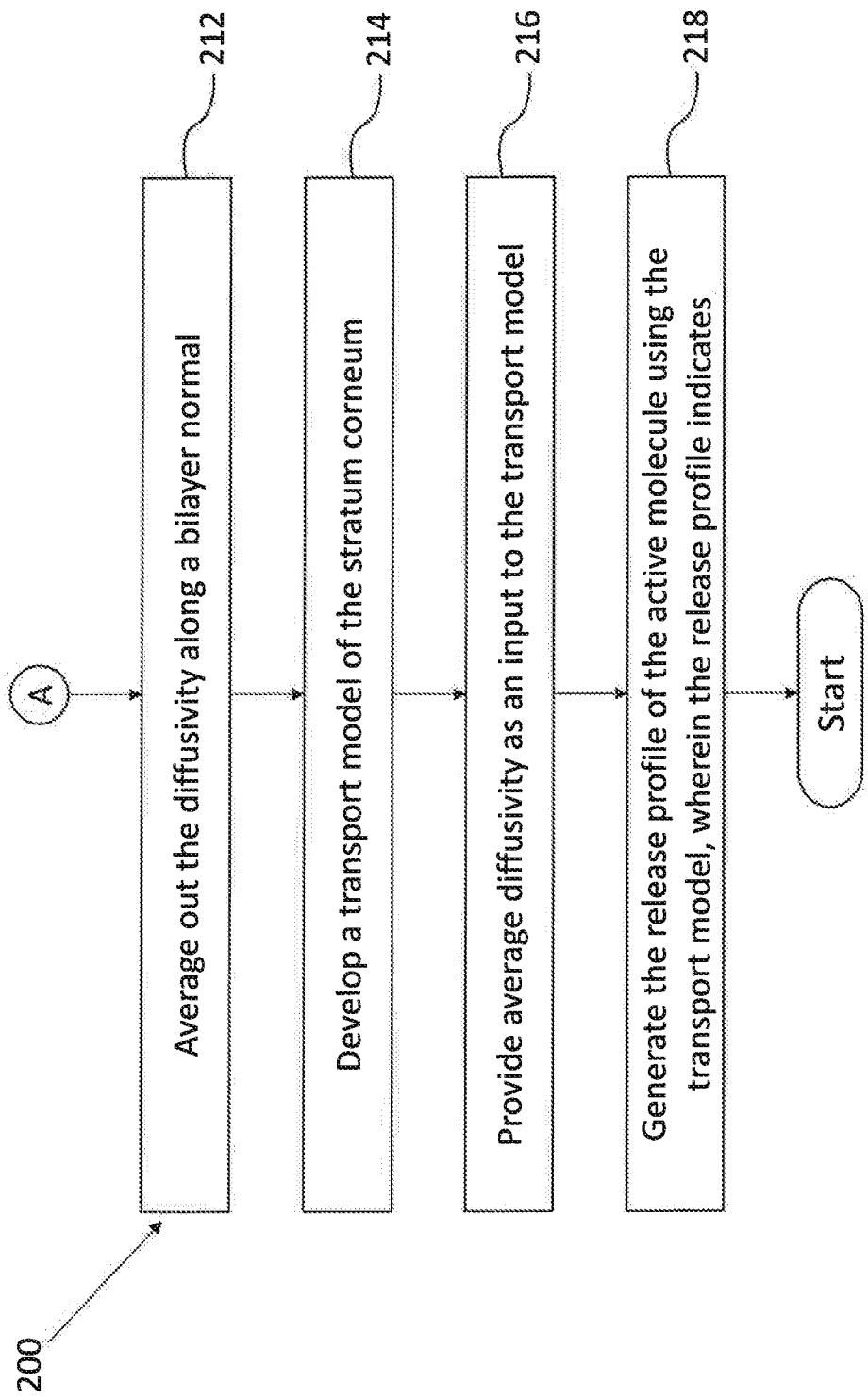
FIG. 2 (CONTD.)

METHOD AND SYSTEM FOR IN SILICO TESTING OF ACTIVES ON HUMAN SKIN

PRIORITY CLAIM

This U.S. patent application claims priority under 35 U.S.C. § 119 to: India Application No. 201721007631, filed on Mar. 3, 2017. The entire contents of the aforementioned application are incorporated herein by reference.

TECHNICAL FIELD

The embodiments herein generally relates to the field of human skin modelling and simulation, and, more particularly, to a method and system for testing of active molecules through developed skin model using molecular dynamics simulations and computational fluid dynamics.

BACKGROUND

Skin, the largest organ of our body protects us from the attack of foreign pathogens and provides barrier to the permeation of many harmful molecules and maintains the hydration level of tissues. The outer layer of skin, also known as Stratum Corneum (SC) is mainly responsible for these barrier properties.

The delivery of drugs through the skin provides a convenient route of administration because of high surface area of skin and can typically be self-administered. The accurate prediction of dermal uptake of chemicals is therefore relevant to both transdermal drug delivery as well as topical application of cosmetics. The main physical property that governs the species transport in the skin is diffusion coefficient. Stratum corneum, the first layer of the skin offers more resistance for permeation. Studying the permeation through stratum corneum is necessary. Stratum corneum consists of corneocytes (dead proteins) and lipid matrix arranged in bricks and mortar fashion respectively. The measurement of the diffusion coefficient of the molecules in stratum corneum is very important in order to predict the transport mechanism. Studying the transport mechanism of molecules through skin is necessary in order to design a new molecule/drugs/cosmetic. The developed molecule is desired to pass the skin layers for drug delivery perspective while penetration inside the skin is not desired for the same in case of cosmetic or skin care application.

The current industry standard, both in pharmaceutical and in cosmetic, is to conduct detailed in-vitro and in-vivo trials on the skin to test any new molecule. These obviously incur huge expenses thereby leading to a very few successful candidates that are finally approved by regulatory authority (FDA). The 2-D in-vitro cell culture studies do not accurately reflect the complex interactions that occur between the multiple cells present in the 3-D in-vivo skin environment. In-vivo studies in rodents and other small animals do not translate well to the human situation due to differences in anatomical structures. Though there are some commercially available human skin equivalents like EpiSkin® (L'Oreal, Paris) and EpiDerm™ (MatTek, Massachusetts), these require highly specialized skills and are very expensive. The European Union (EU) regulation (76/768/EEC, February 2003) prohibits the use of animal or animal-derived substances for the development and testing of cosmetic and pharmaceutical ingredients. The fact that by 2008 only 20 transdermal drug formulations had been approved by FDA substantiates the challenges associated with their development.

Considering the time and costs involved in the development and testing of new drug/cosmetics formulations, it is imperative to replace some of the elaborate in-vivo/in-vitro tests with in-silico tests. Computer simulations offer a way to yield important physical insight at molecular and macroscopic level with an ability to reproduce molecular, bulk and transport properties. Researchers have focused on factorial design of experiments to screen drugs/cosmetics based on their permeability. Most of the Simulation work till now only involved pure Ceramide bilayer which is far from the real skin composition. Earlier simulation works mostly focus on phospholipid cell membranes in liquid crystalline phase which makes sampling easier in MD simulations. The diffusivity, which is a critical parameter for CFD simulation, is generally used from the fitted models. These models mostly derived considering skin as homogeneous membrane.

The current practice is to first carry out permeation experiments and then permeation data is fitted to a known homogeneous model. The fitted diffusion coefficient is an approximate one because it doesn't account for heterogeneity of the stratum corneum lipids. The lipids of skin stratum corneum should be approximated with realistic composition in order to calculate the diffusion coefficient accurately. The calculated diffusion coefficient can further be used to predict the dermal uptake/ cumulative release through the stratum corneum using computational fluid dynamics techniques.

SUMMARY

The following presents a simplified summary of some embodiments of the disclosure in order to provide a basic understanding of the embodiments. This summary is not an extensive overview of the embodiments. It is not intended to identify key/critical elements of the embodiments or to delineate the scope of the embodiments. Its sole purpose is to present some embodiments in a simplified form as a prelude to the more detailed description that is presented below.

In view of the foregoing, an embodiment herein provides a system for in-silico testing of actives using simulations of human skin. The system comprises an input/output interface, a structure library, a force field library, a memory and a processor. The input/output interface provides a skin model of the structure of skin's upper layer as a first input. The structure library provides actives as a second input. The force field library provides force field parameters of the skin model and actives a third input. The processor is in communication with the memory. The processor further configured to receive the first input, the second input and the third input from the input/output interface. The processor further configured to perform the steps of: developing a molecular model of stratum corneum layer of the skin membrane in presence of actives using the first input, the second input and the third input; calculating diffusivity of the actives using multiple molecular dynamic simulation; averaging out the diffusivity along a bilayer normal; developing a transport model of the stratum corneum, wherein the transport model represents the transport mechanism of the actives; providing average diffusivity as input to the transport model; and generating, by the processor, the release profile of the actives using the transport model.

In another embodiment, provides a method for in-silico testing of actives using simulations of human skin. Initially a skin model of the structure of skin's upper layer is provided as a first input to a processor. The actives are provided as a second input to the processor. And the force field parameters of the skin model and actives are provided as a third input to the processor. In the next step, a molecular model of stratum corneum layer of the skin membrane is developed by the processor in presence of actives using the first input, the second input and the third input. In the next step, diffusivity of the actives is calculated using multiple molecular dynamic simulation. In the next step, the diffusivity along a bilayer normal is averaged. In the next step, a transport model of the stratum corneum is developed. The transport model represents the transport mechanism of the actives. The average diffusivity is then provided as input to the transport model. And finally, the release profile of the actives is generated by the processor using the transport model.

In yet another embodiment, provides one or more non-transitory machine readable information storage mediums comprising one or more instructions, which when executed by one or more hardware processors perform actions including providing a skin model of the structure of skin's upper layer as a first input to a processor. Further, providing the actives as a second input to the processor and then providing force filed parameters of the skin model and actives to the processor as third input. Then, developing a molecular model of stratum corneum layer of the skin membrane in the presence of actives using the first input, the second input and the third input. Furthermore, calculating diffusivity of the actives using multiple molecular dynamic simulation. Then, averaging out the diffusivity along a bilayer normal. Further, developing a transport model of the stratum corneum, wherein the transport model represents the transport mechanism of the actives. Furthermore, providing average diffusivity as input to the transport model and generating the release profile of the actives using the transport model.

BRIEF DESCRIPTION OF THE DRAWINGS

The embodiments herein will be better understood from the following detailed description with reference to the drawings, in which.

DETAILED DESCRIPTION

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present disclosure, the preferred, systems and methods are now described.

Some embodiments of this disclosure, illustrating all its features, will now be discussed in detail. The disclosed embodiments are merely exemplary of the disclosure, which may be embodied in various forms.

Before setting forth the detailed explanation, it is noted that all of the discussion below, regardless of the particular implementation being described, is exemplary in nature, rather than limiting.

Figure 1:
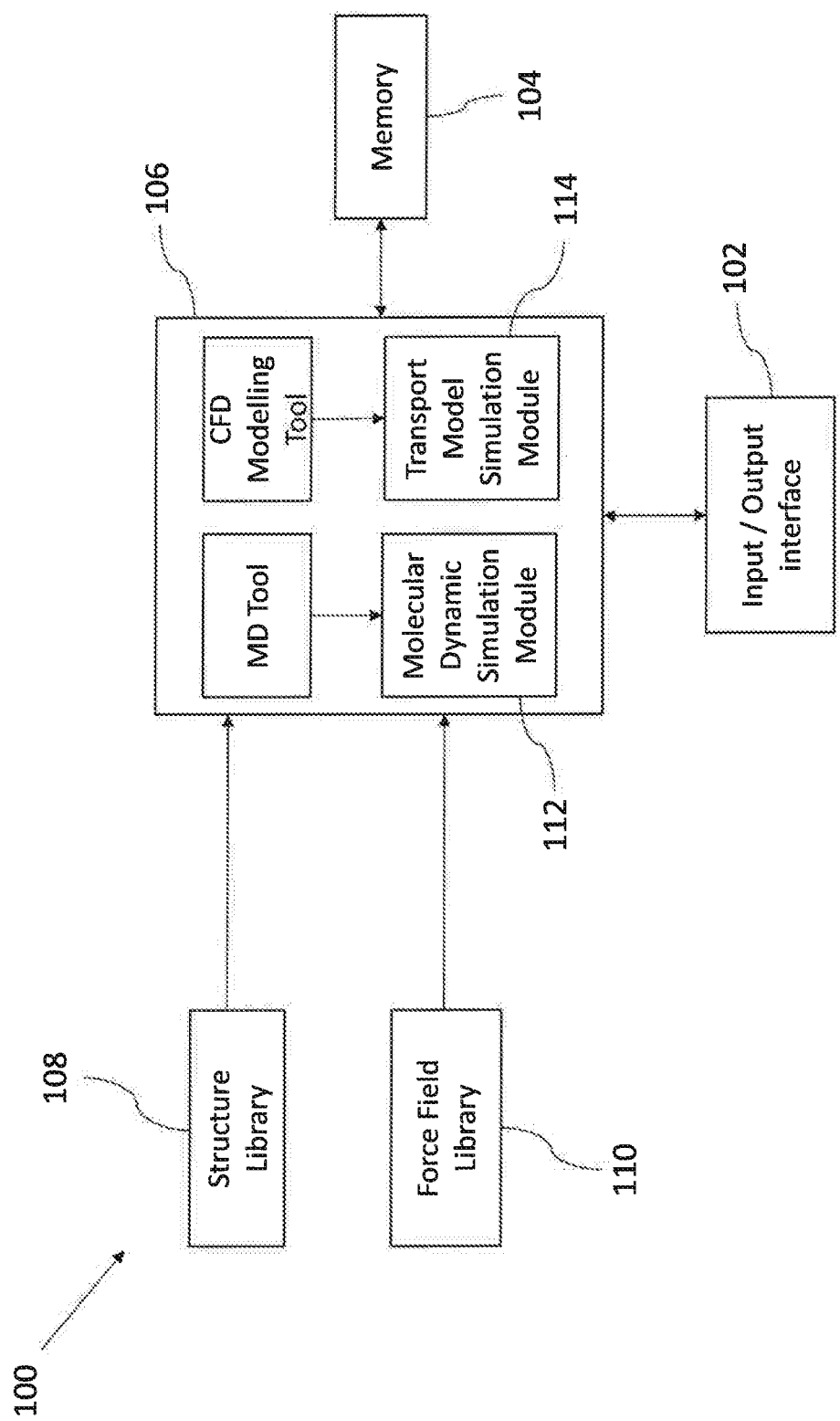
FIG. 1 illustrates a block diagram of a system for in-silico testing of actives using simulations of human skin, in accordance with an embodiment of the disclosure.

Referring now to the drawings, and more particularly to FIG. 1, where similar reference characters denote corresponding features consistently throughout the figures, there are shown preferred embodiments and these embodiments are described in the context of the following exemplary system and/or method.

In the context of the present disclosure, the expression "actives" or "active molecules" refers to the different types of molecules which are going to be used for testing. It should be appreciated that the words actives, active molecules, drugs may be used interchangeably in the description hereunder to represent the testing molecules which are being used in exemplary embodiments.

According to an embodiment of the disclosure, a system 100 for in-silico testing of actives using simulations of human skin is shown in FIG. 1. The disclosure provides a micro and macroscopic level model of the skin's upper protective layer "Stratum-Corneum". The invention presents a multi-scale modeling framework for the calculation of diffusion and release profile of different actives like drugs, particles and cosmetics through developed skin model using molecular dynamics simulations and computational fluid dynamics approach. The systems consist of a molecular model of the skin's upper layer stratum corneum and permeate molecules. The system also consists of a macroscopic transport model of stratum corneum.

The skin model is made up of three most important stratum corneum components namely, Ceramide, cholesterol and free fatty acid. The molecular model employs bonded and non-bonded parameters to describe the interaction between the molecules. Constrained molecular dynamics simulation is used for the calculation of diffusion coefficient. This averaged diffusion coefficient along the bilayer normal is used as an input to the macroscopic model. The macroscopic model is further solved using computational fluid dynamics technique.

According to an embodiment of the disclosure, a block diagram of the system 100 is shown in FIG. 1. The system 100 includes an input/output interface 102, a memory 104 and a processor 106 in communication with the memory 104. The memory 104 is configured to store a plurality of algorithms. The processor 106 further includes a plurality of modules for performing various functions. The plurality of modules access the plurality of algorithms stored in the memory 104 to perform various functions. The system 100 also includes a structure library 108 and a force field library 110.

The I/O interface 102 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server. The input/output interface 102 is configured to provide a skin model of the structure of skin's upper layer as a first input to the processor 106.

According to an embodiment of the disclosure, the system 100 also includes the structure library 108 and the force field library 110. The structure library 108 is a database of different types of actives such as drugs, biomolecules, protein, cosmetics, nanoparticles, skin constituents' solvents etc. The structure library 108 is configured to provide a second input to the processor 106. The force field library 110 comprises various databases such as GROMOS, OPLS, AMBER, CHARMM, COMPASS etc. The force field library 110 is configured to provide a third input to the processor 106.

According to an embodiment of the disclosure, the processor 106 further includes a molecular dynamic simulation module 112 and a transport model simulation module 114. The molecular dynamic simulation module 112 is configured to develop a molecular model of stratum corneum layer of the skin membrane in presence of actives using the first input, the second input and the third input. The multiple molecular dynamic simulations are performed under a constant temperature and pressure. In an example, the simulations are performed at the physiological temperature of 310 K and normal atmospheric condition of 1 atm. Though the simulations can also be performed at any other temperature and pressure but need to be maintained constant. The molecular model of the stratum corneum provides molecular level information of skin lipid matrix as well as the permeation process of the actives. In an example, the system 100 is using GROMOS database for the molecular dynamic simulation.

The skin model is made up of three most important stratum corneum components namely, Ceramide, cholesterol and free fatty acid. The molecular model developed by the molecular dynamic simulation module 112 employs bonded and non-bonded parameters to describe the interaction between the molecules. Constrained multiple molecular dynamics simulation is used for the calculation of diffusion coefficient or diffusivity of the active molecules. The molecular dynamic simulation module 112 is further configured to average out the diffusivity along a bilayer normal. The simulation provides lateral and z direction (along the bilayer normal) diffusion of the actives through the skin lipid matrix.

According to an embodiment of the disclosure, the transport model simulation module 114 develops the transport model of the stratum corneum. The transport model represents the transport mechanism of the actives. The averaged diffusion coefficient along the bilayer normal is further used as an input to the transport model. In an example, finite element technique (FBM) has been used to solve the transport model. Though it should be appreciated that the use of any other numerical technique is well within the scope of this disclosure. The transport model is further configured to generate the release profile of the actives. The diffusivity and release profile of actives determine the permeation property of the actives on the human skin membrane.

Bricks and mortar model is used to represent corneocytes and lipid matrix respectively. The structure is characterized by geometric parameters like corneocytes width, length, thickness of the lipid region, corneocytes offset ratio and number of corneocytes layers. The flux across the SC is measured and integrated with respect to time to calculate the dermal uptake/cumulative release of permeate through SC. The cumulative release is given by the following expression:

$$Q(t) = \int_0^t \frac{\varepsilon}{\tau_{flux}} D_b \left( \frac{\partial C(y, t)}{\partial y} \right)_{y=0} dt$$

Figure 2:
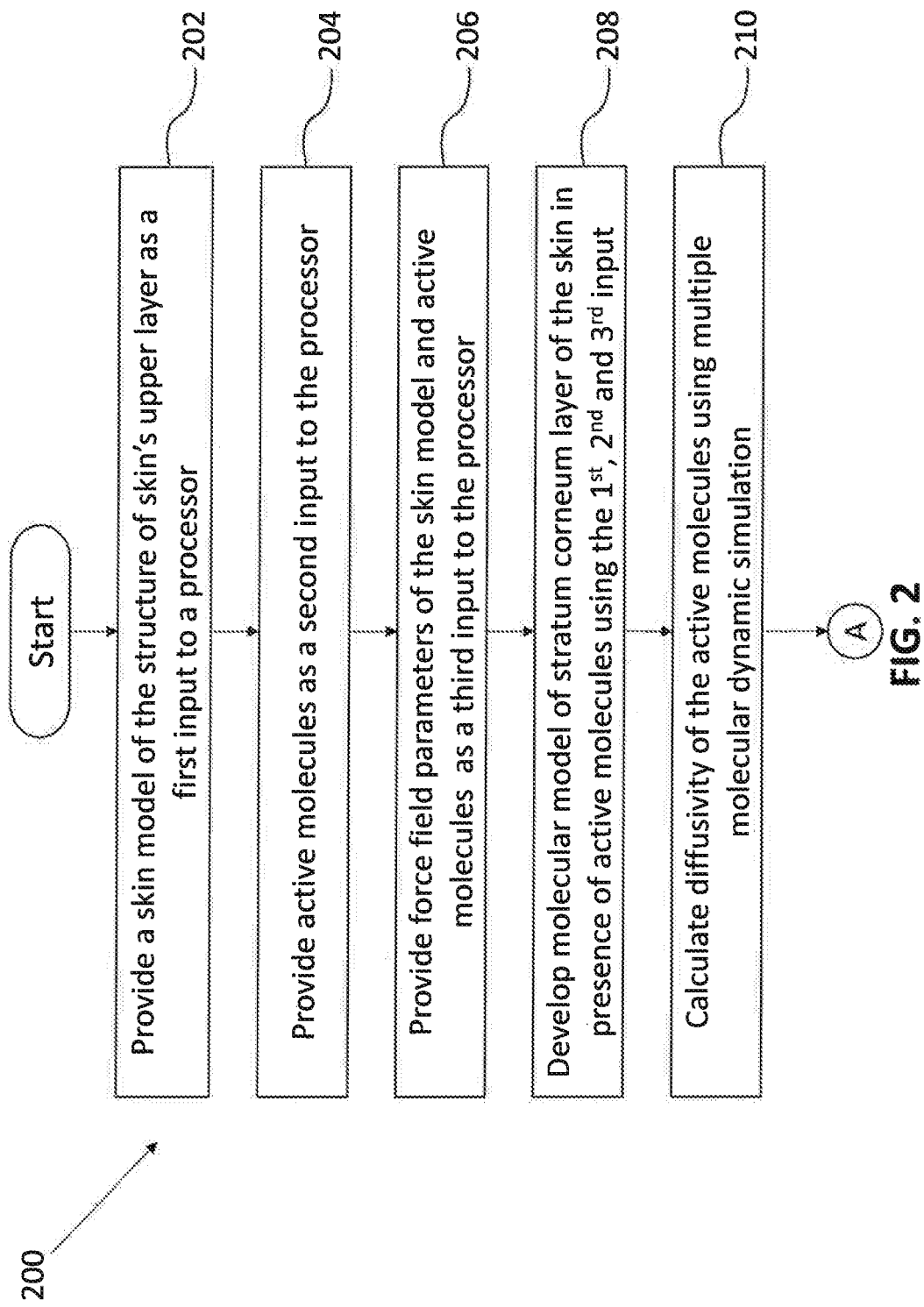
FIG. 2 is a flowchart illustrating the steps involved for in-silica testing of actives using simulations of human skin, in accordance with an embodiment of the disclosure.

In operation, a flowchart 200 for in-silico testing of actives using simulations of human skin is shown in FIG. 2. Initially at step 202, a skin model of the structure of skin's upper layer is provided as a first input to the processor 106. The first input is provided using the input/output interface 102. At step 204, the active molecules are provided as a second input to the processor 106. The active molecules are stored in the structure library. At step 206, the force field parameters of the skin model and active molecules are provided as a third input to the processor 106. The force field parameters are stored in the force field library 110. The force field parameters contain both bonded and non-bonded interaction parameters which are used in running the molecular dynamic simulation. They can have different mathematical form like harmonic, combinations of cosines and sines, exponentials, etc.

At the next step 208, a molecular model of stratum corneum layer of the skin membrane is developed by the processor 106 in presence of actives using the first input, the second input and the third input. At step 210, the diffusivity of the actives is calculated using multiple molecular dynamic simulation. At step 212, the diffusivity along a bilayer normal is averaged out. At step 214, the transport model of the stratum corneum is developed by the processor 106. The transport model represents the transport mechanism of the active molecule. In an embodiment, finite element technique (FEM) has been used to solve the transport model. Though it should be appreciated that the use of any other numerical technique is well within the scope of this disclosure. At the next step 216, the average diffusivity is provided as input to the transport model. And finally at step 218 and the release profile of the active molecules is generated by the processor 106 using the transport model.

According to an embodiment of the disclosure, the system 100 is also configured to compare or validate the release profile of the actives with an experimental release profile of the actives.

According to an embodiment of the disclosure, the method of in-silico testing of actives using simulations of human skin were validated with the help of following experimental findings. The present skin bilayer model was first tested with the experimental data and diffusivity was calculated. This diffusivity compared with the experimental data and used as an input in transport model simulation. The final cumulative release profile of the drug molecule through this virtual skin was compared with the experimental release profile as follows:

Molecular Simulation

Force Field

The force field parameters for the Ceramide were taken from the Berger force field and GROMOS87 parameters. The Ryckaert-Bellemans dihedral potential was used for the hydrocarbon chains of free fatty acids and Ceramide. The parameters for free fatty acid and cholesterol were taken from the GROMOS data set. The simple point charge (SPC) model was used for water molecule.

Simulation setup

The simulations were carried out in NVT and NPT ensemble. The temperature was controlled at 310 K by Nose-Hoover thermostat with a time constant of 5 ps and thermostat coupled separately to lipid molecules and water. Pressure was controlled at 1 bar by Parrinello-Rahman barostat with a time constant of 5 ps and compressibility of 4.5×10-5 bar with semi isotropic coupling (XY and Z direction coupled separately). All the bonds in lipid and solute molecules were constrained using LINCS algorithm while SETTLE algorithm was used for water. A time step of 2 fs was used for all simulations. A cut off of 1.2 nm was used for Vander Wall and electrostatic interactions. All the systems were equilibrated for at least ~5 ns. The final 25 ns run of constrained simulation was used to calculation of constrained force and other properties.

The equi-molar bilayer structure equilibrated for ~200 ns in NPT ensemble. The equi-molar bilayer is made up of 52 CER, 52 CHOL, 52 FFA and 5120 water molecules. The reaction coordinate of the system was chosen to be membrane normal z, where z=0 nm is correspond to the center of mass (COM) of the bilayer. For each system four drug molecules placed manually at different XY plane and Z distance of 4.8 from the COM of the bilayer. Overlapped water molecules were removed and system was then energy minimized. Each system was then equilibrated in NPT ensemble for another 20 ns by keeping solute molecules fixed at their positions. These equilibrated structures were further used for the preparation of the initial configuration of constrained simulations. Solutes were pulled slowly with different velocity towards the center of bilayer. The time step for this run was kept at 1 fs. As the z distance between the center of mass (COM) of the lipid and solute molecule changes by 0.2 nm, the configuration was stored. In each window drug molecules were constrained at different Z and XY position. Total 25 windows were generated using the above procedure. These windows span the whole space from the bulk water from upper leaflet to the middle of the bilayer. To stop the interaction in between the solutes which are in the same window, the minimum z distances were kept as 1.2 nm (cut off for vdW and coulomb).

The stored equidistance configuration was further run for 30 ns out of which first 5 ns simulation was discarded as an equilibration run. The distance between the COM of solute and COM of bilayer was constrained in z direction while solute was free to move in lateral direction. The configuration was stored at every 1 ps and constrained force was stored at every 10 fs. Last 25 ns runs of each simulation were used to calculate diffusion and potential of mean force. It was assumed that bilayer is symmetric and result from the one side of bilayer will be the mirror image of the result of other side.

Local Diffusion Coefficient

The homogenous solubility diffusion model is generally used for the calculation of passive permeability of solutes through membranes. According to this model the solute first dissolves into the membrane, then diffuses through the membrane interior, and finally dissolves again in the outer surrounding medium. The permeability for this model is given by $$p = \frac{KD}{d}$$

Where p is the permeability of the molecules across the bilayer, K is the solute partition function from aqueous to organic phase, D is the diffusion coefficient of solute and d is the thickness of the bilayer. This model has been challenged many times. It has been shown previously that solute size and composition changes the permeability many folds as well as local partition function governs the solute permeability. Molecular dynamics simulation provides attractive way to calculate D(z) along the bilayer normal z. We have adopted nonhomogeneous solubility diffusion model to compute the diffusivity.

The diffusivity of a molecules in a symmetric bilayer system which has normal in z direction can be given by $$D(z) = \frac{(RT)^2}{\int_0^\infty (\Delta F(z, t) \Delta F(z, 0)) > dt}$$

$$\Delta F(z, t) = F(z, t) - < F(z, t) >$$

Where R is gas constant, T is temperature, F (z,t) is constrained force on solute at a given z.

Computational Fluid Dynamics Model

The modified Fick's 2nd law is solved in the lipid region of SC with the boundary conditions in FEM framework.

$$\frac{\partial C}{\partial t} = \left(\frac{Db}{\tau_{flux} \tau_{volume}}\right) \nabla^2 C$$

Where, C=concentration of permeant,
Db=Diffusion coefficient of permeant in lipid region of SC
$T_{flux}$, $T_{volume}$=tortuosity factors to account for parallel and branched transport or permeant in lipid region,
t=time.
$T_{flux}$, $T_{volume}$ are calculated from the geometric parameters of SC $$|\tau_{volume} = \frac{Nh + (N-1)g + (N-1)d}{Nh + (N-1)g}$$

$$\tau_{flux} = \frac{Nh + (N-1)g + (N-1)\frac{\omega}{(1+\omega)^2}d}{Nh + (N-1)g}$$

Where, h=Corneocyte width,
d=Corneocyte length,
g=Lipid channel thickness,
ω=Corneocyte offset ratio,
N=Number of Corneocyte layers in SC.

Bricks and mortar model is generally used to represent corneocytes and lipid matrix respectively. The structure is characterized by geometric parameters like corneocyte width, length, thickness of the lipid region, corneocyte offset ratio and number of corneocyte layers. The flux across the SC is measured and integrated with respect to time to calculate the dermal uptake/cumulative release of permeant through SC. The cumulative release is given by the following expression $$Q(t) = \int_0^t \frac{\varepsilon}{\tau_{flux}} D_b \left(\frac{\partial C(y, t)}{\partial y}\right)_{y=0} dt$$

Simulation Setup

Figure 3:
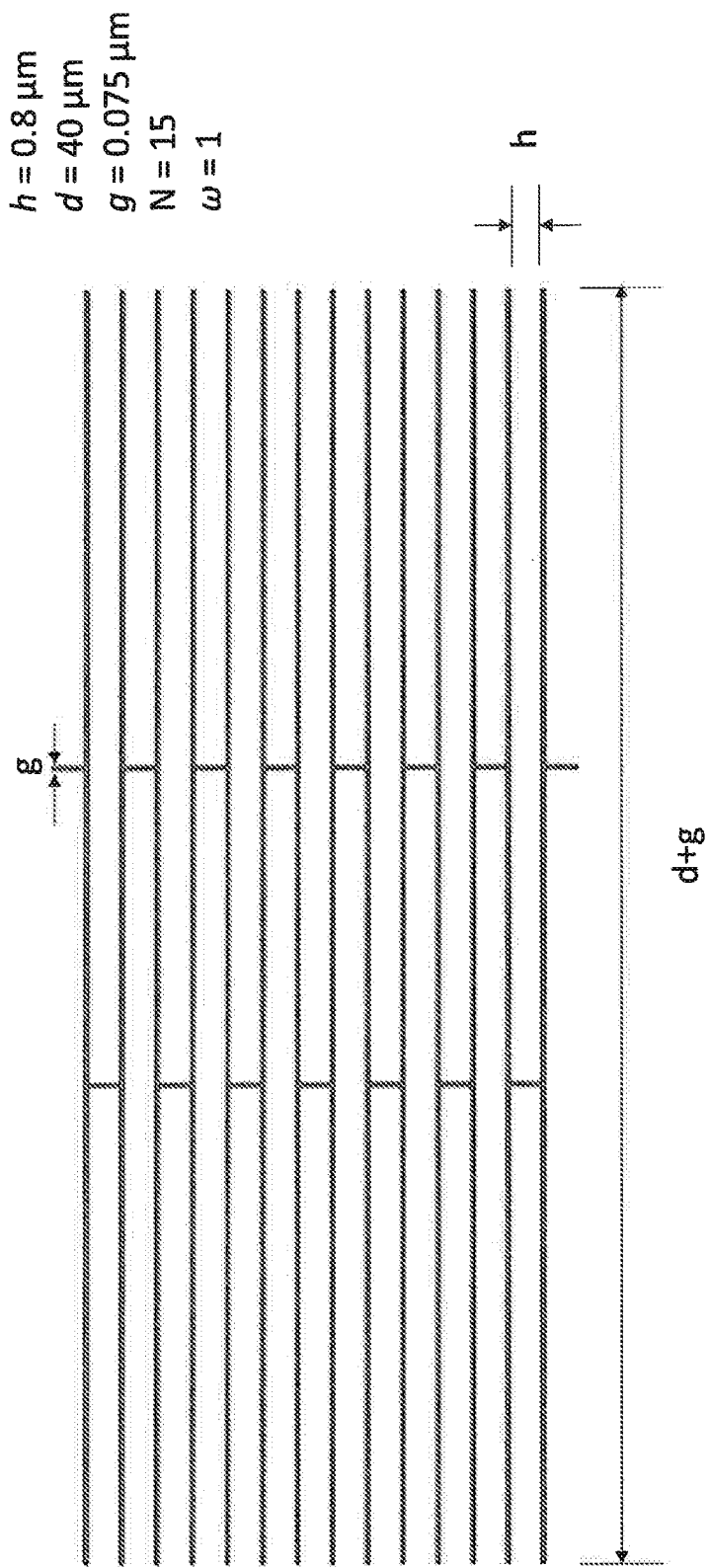
FIG. 3 shows the geometry of skin upper layer stratum corneum created using brick and mortar model, in accordance with an embodiment of the disclosure.
Figure 4:
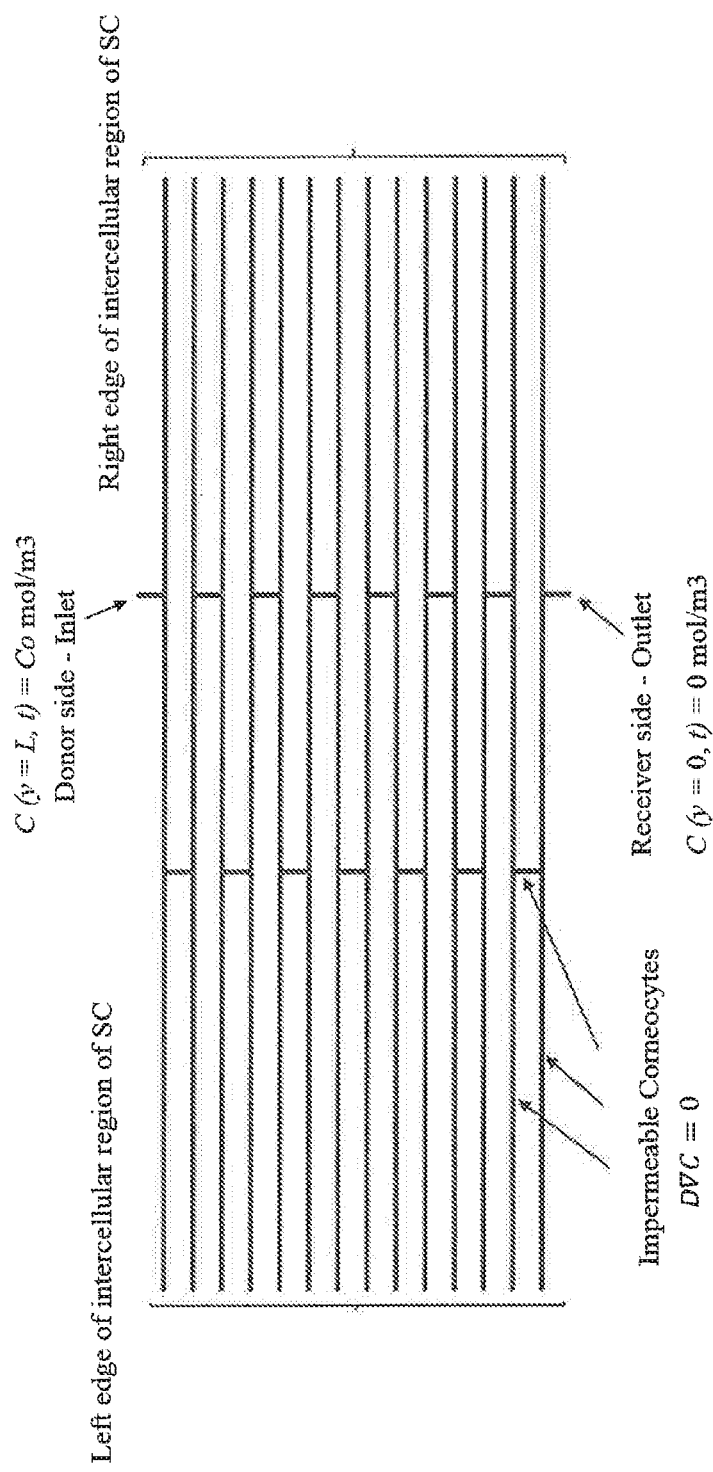
FIG. 4 shows initial and boundary conditions across the stratum corneum layer used in the computational fluid dynamics simulation data, in accordance with an embodiment of the disclosure.

The geometric parameters are obtained from the literature. h=0.8 μm, d=40 μm, g=0.075 μm, ω=1, N=15. Based on these parameters the geometry was created as shown in FIG. 3. Geometry is meshed with triangular elements. The simulations are performed in COMSOL multiphysics. The following boundary condition are used for CFD simulation as shown in FIG. 4.
Concentration at inlet (donor side) C (t, y=L)=Co mol/m3,
Concentration at outlet (receiver side) C (t, y=0)=0 mol/m3,
Initial concentration in the lipid region of SC C (t=0)=0 mol/m3,
Periodic boundary condition at both sides of lipid region of SC.

System parameters

The permeant studied in here is fentanyl. The concentration of fentanyl is 0.09 mol/m3. The partition coefficient of fentanyl from the patch to SC is 0.14. The diffusivity of fentanyl is calculated from molecular dynamics simulation (Db=3.67×10-10 m2/s). The CFD simulations are run for time of 70 hours with time step of 100 s.

RESULTS

Figure 5:
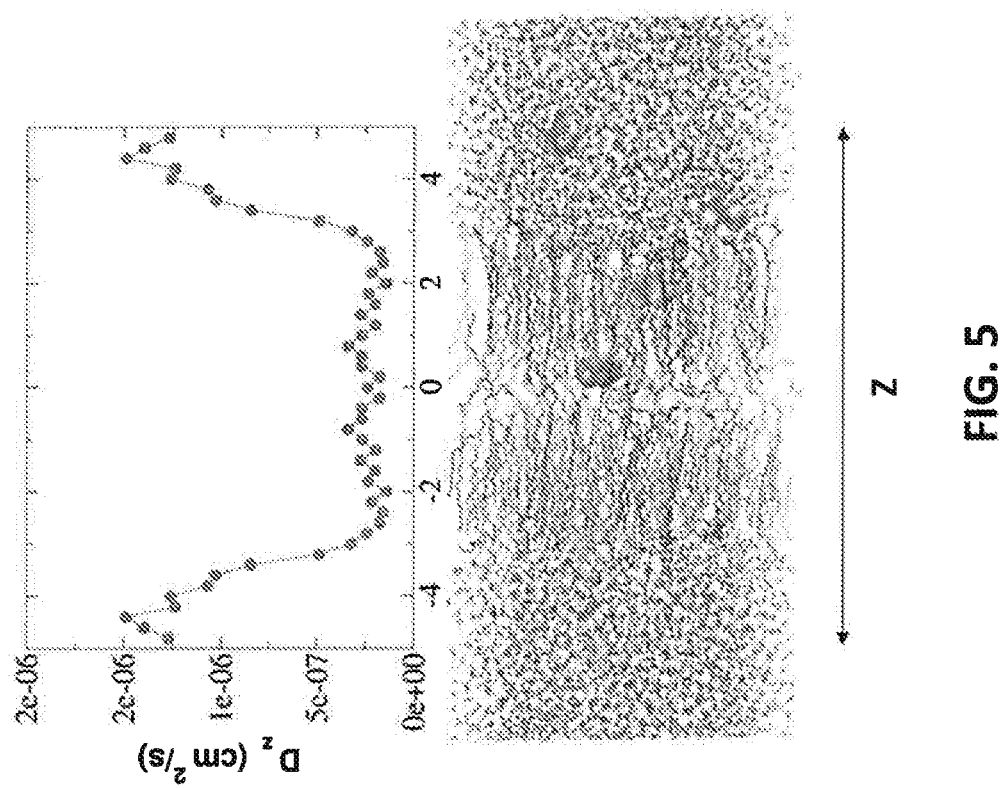
FIG. 5 shows local diffusion coefficient of fentanyl molecule calculated from the constrained molecular dynamics simulations in accordance with an embodiment of the disclosure.
Figure 6:
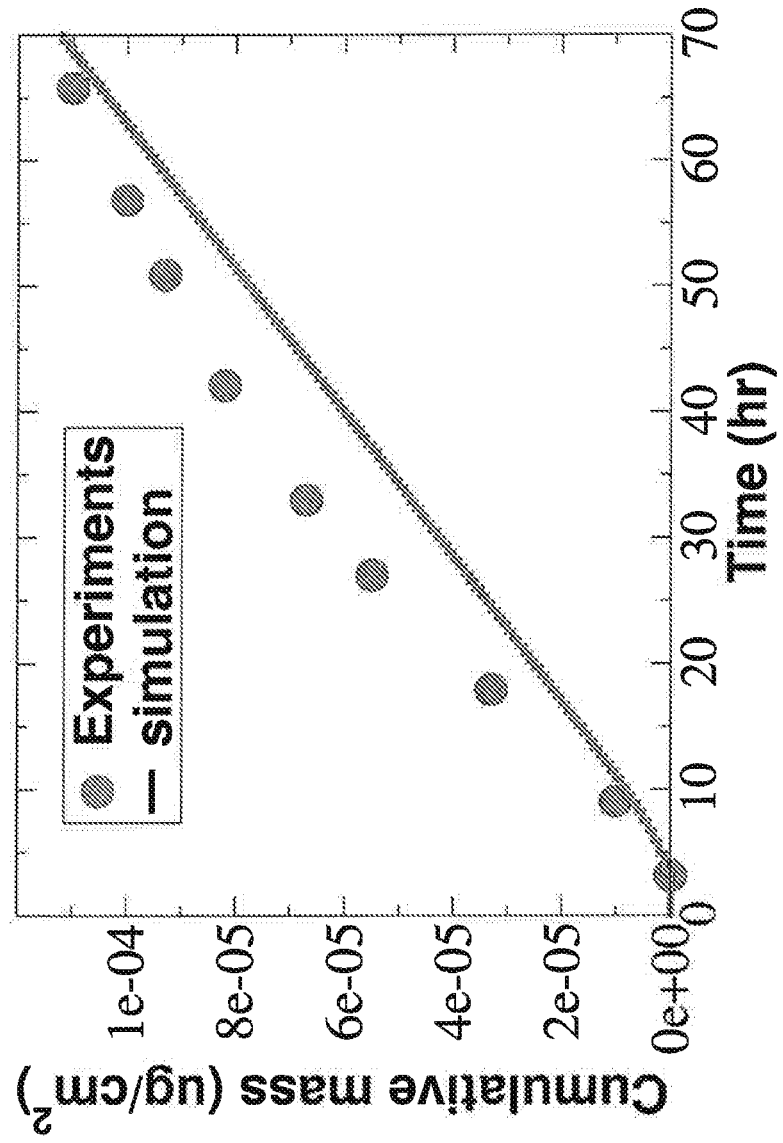
FIG. 6 shows cumulative mass release profile of Fentanyl calculated using multi-scale modeling framework protocol, in accordance with an embodiment of the disclosure.

Unlike the homogenous diffusion model of bilayer, the diffusion coefficient was found to be bilayer depth dependent as shown in FIG. 5.
The diffusion coefficient in bulk water was found to be higher as compared to the interior of the bilayer as shown in FIG. 5. This might because of less free volume in the interior of the bilayer.
The diffusion coefficient in bulk water for fentanyl drug was found to be $(1.8\pm0.3)\times10^{-6}$ cm$^2$/s as shown in FIG. 5.
Diffusion inside the bilayer decreased by almost an order as compare to the bulk value for fentanyl drug molecule as shown in FIG. 5.
The averaged diffusion coefficient of fentanyl drug calculated along the bilayer depth was found to be $3.67\times10^{-6}$ cm$^2$/s.
The dermal uptake/cumulative release of permeant fentanyl through SC layer was found to be well in agreement with the reported experimental profiles as shown in FIG. 6.
The developed multi-scale modeling framework could be used for the screening/testing of any drug/cosmetic/biomolecules etc. on skin SC.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

A representative hardware environment for practicing the embodiments may include a hardware configuration of an information handling/computer system in accordance with the embodiments herein. The system herein comprises at least one processor or central processing unit (CPU). The CPUs are interconnected via system bus to various devices such as a random access memory (RAM), read-only memory (ROM), and an input/output (I/O) adapter. The I/O adapter can connect to peripheral devices, such as disk units and tape drives, or other program storage devices that are readable by the system. The system can read the inventive instructions on the program storage devices and follow these instructions to execute the methodology of the embodiments herein.

The system further includes a user interface adapter that connects a keyboard, mouse, speaker, microphone, and/or other user interface devices such as a touch screen device (not shown) to the bus to gather user input. Additionally, a communication adapter connects the bus to a data processing network, and a display adapter connects the bus to a display device which may be embodied as an output device such as a monitor, printer, or transmitter, for example. The preceding description has been presented with reference to various embodiments. Persons having ordinary skill in the art and technology to which this application pertains will appreciate that alterations and changes in the described structures and methods of operation can be practiced without meaningfully departing from the principle, spirit and scope.

We claim:

1. A method for in-silico testing of actives using simulations of human skin, the method comprising:
   providing a skin model of the structure of stratum corneum as a first input to a processor;
   providing the actives as a second input to the processor;
   providing force field parameters of the skin model and actives as a third input to the processor, wherein the force field parameters include at least one of bonded and non-bonded interaction parameters to run a molecular dynamic simulation;
   developing, by the processor, a molecular model of stratum corneum layer of the skin membrane in presence of actives using the first input, the second input and the third input, wherein the molecular model of the stratum corneum provides molecular level information of a skin lipid matrix and permeation process and wherein constrained multiple molecular dynamic simulation is used to calculate diffusion coefficient or diffusivity of the actives;
   calculating, by the processor, the diffusivity of the actives using multiple molecular dynamic simulation, wherein the molecular dynamic simulation enables calculation of a diffusion coefficient, and wherein the molecular dynamic simulation provides lateral and z direction diffusion of the actives through the skin lipid matrix;
   averaging out the diffusivity along the stratum corneum, wherein the diffusivity and release profile of actives determine a permeation property of actives on the human skin membrane;
   developing, by the processor, a transport model of the stratum corneum, using computational fluid dynamics technique, wherein the transport model represents the transport mechanism of the actives, wherein averaged diffusion coefficient along a bilayer normal is used as an input to the transport model;
   providing average diffusivity as input to the transport model; and
   generating, by the processor, the release profile of the actives using the transport model.

2. The method of claim 1, further comprising comparing the release profile of the actives with an expeRimental release profile of the actives.

3. The method of claim 1, wherein the actives comprise at least one of a drug, biomolecule, protein, nanoparticle, cosmetic, or a solvent.

4. The method of claim 1, wherein the molecular model of stratum corneum layer of the skin membrane is made up of Ceramide, cholesterol and free fatty acids.

5. The method of claim 1, wherein the transport model is made using brick and mortar geometry for stratum corneum of the skin.

6. The method of claim 1, wherein the multiple molecular dynamic simulations are performed under constant temperature and pressure.

7. The method of claim 1, wherein the diffusivity of the actives along the bilayer normal is considered in the transport model.

8. A system for in-silico testing of actives using simulations of human skin, the system comprising:
   an input/output interface configured to provide a skin model of the structure of stratum corneum as a first input;
   a structure library for providing actives as a second input;
   a force field library for providing force field parameters of the skin model and actives a third input, wherein the force field parameters include at least one of bonded and non-bonded interaction parameters to run a molecular dynamic simulation;
   a memory; and
   a processor in communication with the memory, wherein the processor configured to receive the first input, the second input and the third input from the input/output interface, the processor further configured to perform the steps of:
      developing a molecular model of stratum corneum layer of the skin membrane in presence of actives using the first input, the second input and the third input, wherein the molecular model of the stratum corneum provides molecular level information of a skin lipid matrix and permeation process and wherein constrained multiple molecular dynamic simulation is used to calculate diffusion coefficient or diffusivity of the actives;
      calculating the diffusivity of the actives using multiple molecular dynamic simulation, wherein the molecular dynamic simulation enables calculation of a diffusion coefficient, and wherein the molecular dynamic simulation provides lateral and z direction diffusion of the actives through the skin lipid matrix;
      averaging out the diffusivity along the stratum corneum, wherein the diffusivity and release profile of actives determine a permeation property of actives on the human skin membrane;
      developing a transport model of the stratum corneum using computational fluid dynamics technique, wherein the transport model represents the transport mechanism of the actives, wherein averaged diffusion coefficient along a bilayer normal is used as an input to the transport model;
      providing average diffusivity as input to the transport model; and
      generating, by the processor, the release profile of the actives using the transport model.

9. The system of claim 8, wherein the transport model is a macroscopic model.

10. The system of claim 8, wherein the actives comprise at least one of a drug, biomolecule, protein, nanoparticle, cosmetic, or a solvent.

11. The system of claim 8, wherein the molecular model of stratum corneum layer of the skin membrane is made up of Ceramide, cholesterol and free fatty acids.

12. The system of claim 8, wherein the transport model is made using brick and mortar geometry for stratum corneum of the skin.

13. One or more non-transitory machine readable information storage mediums comprising one or more instructions which when executed by one or more hardware processors perform actions comprising:

providing a skin model of the structure of stratum corneum as a first input to a processor;

providing the actives as a second input to the processor;

providing force field parameters of the skin model and actives as a third input to the processor, wherein the force field parameters include at least one of bonded and non-bonded interaction parameters to run a molecular dynamic simulation;

developing, by the processor, a molecular model of stratum corneum layer of the skin membrane in presence of actives using the first input, the second input and the third input, wherein the molecular model of the stratum corneum provides molecular level information of a skin lipid matrix and permeation process and wherein constrained multiple molecular dynamic simulation is used to calculate diffusion coefficient or diffusivity of the actives;

calculating, by the processor, diffusivity of the actives using multiple molecular dynamic simulation, wherein the molecular dynamic simulation enables calculation of a diffusion coefficient, and wherein the molecular dynamic simulation provides lateral and z direction diffusion of the actives through the skin lipid matrix;

averaging out the diffusivity along the stratum corneum, wherein the diffusivity and release profile of actives determine a permeation property of actives on the human skin membrane;

developing, by the processor, a transport model of the stratum corneum using computational fluid dynamics technique, wherein the transport model represents the transport mechanism of the actives, wherein averaged diffusion coefficient along a bilayer normal is used as an input to the transport model;

providing average diffusivity as input to the transport model; and generating, by the processor, the release profile of the actives using the transport model.

14. The one or more non-transitory machine readable information storage mediums of claim 13, further comprising comparing the release profile of the actives with an expeRimental release profile of the actives.

15. The one or more non-transitory machine readable information storage mediums of claim 13, wherein the actives comprise at least one of a drug, biomolecule, protein, nanoparticle, cosmetic, or a solvent.

16. The one or more non-transitory machine readable information storage mediums of claim 13, wherein the molecular model of stratum corneum layer of the skin membrane is made up of Ceramide, cholesterol and free fatty acids.

17. The one or more non-transitory machine readable information storage mediums of claim 13, wherein the transport model is made using brick and mortar geometry for stratum corneum of the skin.

18. The one or more non-transitory machine readable information storage mediums of claim 13, wherein the multiple molecular dynamic simulations are performed under constant temperature and pressure.

19. The one or more non-transitory machine readable information storage mediums of claim 13, wherein the diffusivity of the actives along the bilayer normal is considered in the transport model.

* * * * *